United States Patent [19]

Youdelis

[11] 4,181,757
[45] Jan. 1, 1980

[54] PROCESS FOR SURFACE COATING GOLD ALLOYS ONTO A METALLIC SUBSTRATE TO ENHANCE CORROSION PROTECTION

[76] Inventor: William V. Youdelis, 1935 W. Grand Blvd., Windsor, Ontario, Canada, N9E 1G6

[21] Appl. No.: 870,232

[22] Filed: Jan. 17, 1978

[30] Foreign Application Priority Data

Oct. 27, 1977 [CA] Canada .................................. 289645

[51] Int. Cl.² ............................................. B05D 3/02
[52] U.S. Cl. .................................. 427/229; 106/1.18; 75/165; 427/2; 427/310; 427/383 C; 427/383 D
[58] Field of Search .................. 427/2, 383 C, 383 D, 427/310, 229, 191; 428/672; 75/165; 106/1.18

[56] References Cited

U.S. PATENT DOCUMENTS

| 2,980,998 | 4/1961 | Coleman et al. | 75/165 |
| 3,199,189 | 8/1965 | La Plante | 428/672 |
| 3,367,756 | 2/1968 | La Plante | 428/672 |
| 3,574,610 | 4/1971 | Prosen | 75/165 |
| 3,684,533 | 8/1972 | Conwicke | 106/1.14 |
| 3,901,693 | 8/1975 | Wolf | 428/672 |
| 3,915,729 | 10/1975 | Eustice | 148/23 |

FOREIGN PATENT DOCUMENTS

641525 8/1950 United Kingdom .

Primary Examiner—John D. Smith
Attorney, Agent, or Firm—Beveridge, DeGrandi, Kline & Lunsford

[57] ABSTRACT

Processes and compositions are disclosed for surface coating of metals and alloys of low nobility with gold alloys to provide improved corrosion resistance and surface hardness to the underlying metals.

11 Claims, 2 Drawing Figures

MAGNIFICATION X 8

MAGNIFICATION X 200

PROCESS FOR SURFACE COATING GOLD ALLOYS ONTO A METALLIC SUBSTRATE TO ENHANCE CORROSION PROTECTION

This invention relates to processes and compositions for surface coating of metals and alloys of low nobility with low-melting-temperature gold alloys to impart an improved corrosion and tarnish resistance to the underlying or parent metal which approaches that of pure gold, as well as providing a surface hardness that is equal to or surpasses that of many heat-treatable gold alloys.

Alloys which are used for dental prostheses such as inlays, crowns, bridges and partial dentures, must provide several essential properties which include good casting ability, ease of fabricating, corrosion resistance and hardness. These properties are developed best in alloys of high precious metal content; however, even high precious metal content alloys fail to satisfactorily meet all of the clinical requirements in all applications, in particular hardness, which decreases as the gold content is increased to meet the required corrosion resistance. There is thus a need, particularly for dental work, to provide materials with good casting and working properties while still retaining good hardness and corrosion resistance.

It is an object of the present invention to provide a process and materials or compositions therefor, for coating metal surfaces with low-melting-temperature gold alloys, which are differentiated from electroplating with pure gold, to impart high corrosion resistance and surface hardness to the underlying or parent metal which has a lower corrosion resistance and hardness. The underlying or parent metal may be chosen to take advantage of certain specific characteristic properties, e.g. ability to be easily cast and the ability to be easily fabricated as well as low cost, with the required corrosion resistance being provided by a thin surface layer of gold alloy which is integrally bonded to the underlying or parent material.

By the present teachings, a process has been developed for integrally bonding a layer of low-melting-temperature gold alloy of controlled thickness onto the surface of less noble metals that is particularly suited to alloys such as silverbase or copper-base alloys. By the present process surface details of the underlying metal are accurately reproduced provided that the gold alloy layer deposited in one application does not exceed about 100 to 150 microns in thickness. The surface corrosion resistance obtained is equivalent to that of the gold alloy employed for the coating; however, the corrosion resistance is noted to decrease with depth into the coating due to increasing alloying of the surface layer with the underlying or parent metal.

The preferred process for coating the underlying or parent metal with the protective gold alloy may be as follows:

(a) coating as by brushing, painting, spraying, etc., the surface of the parent metal with a slurry composed of a low-melting-temperature gold alloy powder, an essentially inorganic oxide-dissolving flux which becomes fully active at above about 550° C. and an organic liquid; and (b) firing the slurry coating to a temperature at about 540° C. and above to melt and spread the gold alloy contained in the slurry over the parent metal surface. The heat may be applied employing an open gas flame i.e. a Bunsen burner, propane torch etc. or may be applied by an electric or induction furnace.

The slurry which is coated onto the parent metal is composed essentially of three major constituents: a low-melting-temperature gold alloy powder, an oxide-dissolving flux powder or emulsion and an organic liquid which is the vehicle for spreading the gold alloy and flux particles over the parent metal surface. The gold alloy should be in particular form and preferably pass through a 400 mesh screen (or finer) to facilitate the application of a slurry layer of uniform thickness.

The preferred low-melting temperature gold alloy for the coating material is a eutectic or near eutectic gold-germanium alloy containing about 88% gold and about 12% germanium by weight. Other gold alloys which may be employed are the eutectic alloys of gold-silicon and gold-tin, containing respectively about 94% gold and about 6% silicon by weight and about 80% gold and about 20% tin by weight. The melting temperatures of these eutectic gold alloys are about 356° C. for the gold-germanium, approximately 370° C. for the gold-silicon and about 280° C. for the gold-tin alloy. A combination of any two or three of these eutectic alloys may also be employed as the coating material.

The slurry also contains an oxide-dissolving flux and the role of the flux in the slurry is to dissolve surface oxides and increase the wetting and spreading action of the liquefied gold alloy. For applying coatings to silver-base and copper-base alloys several commercially available brazing fluxes are suitable for this purpose, e.g. Handy Flux, manufactured by Handy and Harman, the principal oxide-dissolving ingredients in these fluxes being borates, carbonates, fluorides and chlorides of the alkali metals sodium and potassium and the fluxes become fully active in a temperature range of about 550°–600° C.

The flux may be employed in powder form and may be either admixed with the gold alloy powder or the flux may be incorporated into the organic liquid vehicle. When added to the gold alloy powder about 2% by weight of flux is sufficient. On the other hand, when the flux is incorporated into the organic liquid about 15% by weight would be required. It should be noted that it is important to avoid adding too much flux in view that bubbling and rising of the slurry layer may become excessive when fired due to evolution of water of hydration from the flux constituents.

The organic fluid for the slurry is employed as a vehicle for spreading the gold powder and flux particles over the surface of the underlying or parent metal. The vapor pressure of the organic fluid should be sufficiently high so that the slurry will dry relatively quickly when applied by brush or spray. The liquid should also have some water solubility otherwise the flux particles may tend to agglomerate. High vapor pressure liquids have correspondingly low boiling points, and there are several organic liquids which would have boiling points below that of water (100° C.) and are also water soluble to some degree. The preferred organic liquid vehicle is a mixture of three liquid organic constituents and is composed of about 1 part of ethylene glycol, about one part cyclohexanol and about one part ethyl or methyl alcohol by volume.

Thus, in accordance with the present teachings, in addition to the process of coating there is also provided a powder composite composed of about 1 to 5% by weight of a flux powder containing oxide-dissolving constituents and the remaininder a gold alloy powder, the gold alloy powder being about 88% gold and about 12% germanium by weight. In a further aspect of the invention there is also provided an organic liquid to function as a vehicle for applying gold alloy and flux powder constituents onto the underlying or parent metal surface, the organic liquid being composed of about 1 part ethylene glycol, about one part of cyclohexanol, and about 1 part ethyl or methyl alcohol by volume.

The gold alloy-flux powder composite together with the organic liquid may be mixed in such proportions as to provide a slurry of desired fluidity for brushing or spraying onto the underlying or parent metal surface.

After the application of the slurry to the underlying or parent metal surface, heat is then applied to melt the slurry coating and to spread the gold alloy over the surface of the metal. This heating may be accomplished by an open gas flame or by a furnace. No special precautions are necessary against oxidation during firing although a reducing or inert atmosphere may be preferred. If the slurry coated underlying or parent metal is heated over an open gas flame, such as a Bunsen burner or propane torch, the heat should be applied slowly and uniformly by continually moving the flame over the whole surface to avoid localized overheating, otherwise lifting or spalling of the slurry coating may result due to a too rapid vaporization and effusion of the organic constituents. For the fluxes and gold alloy compositions of the present concept, a temperature of about 600° C. is adequate to melt and spread the alloy and should not be exceeded. With experience, an operator can readily estimate when the required temperature is attained by the "flash" or rapid spreading of the gold alloy over the surface. After the flash has occurred the flame should then be removed to avoid excessive heating or alloying of the gold alloy with the underlying or parent metal.

The slurry coating which has been applied to the underlying or parent metal may also be fired in an electric or induction furnace under more precisely controlled conditions. Again, heat must not be applied too rapidly in order to avoid excessive lifting or localized spalling of the slurry coating. When an electric resistance furnace is used a recommended procedure which may be followed is to place the slurry-coated underlying or parent metal into the furnace chamber, which is at a temperature of about 540° C. but not exceeding 560° C., maintain the temperature for 3 to 5 minutes and then raise the temperature to about 600° C. which would require up to about 5 minutes. The temperature of 600° C. is then held for an additional 3 to 5 minutes and the composite is then removed and quenched in water. The total elapsed furnace time should run about 10 to 15 minutes. During the initial 3 to 5 minute period at 540° to 560° C. the flux in the slurry coating slowly liquifies with a minimum of rising and bubbling and removes any surface oxides as it spreads over the surface of the underlying or parent metal. The gold alloy powder also liquifies and spreads over the surface at the same time. The latter 3 to 5 minute period in the furnace held at a temperature of about 600° C. ensures completion of the spreading of the liquid gold alloy by surface tension forces.

The thickness of the gold alloy coatings may readily be controlled by varying the thickness of the slurry coating with a continuous layer of gold alloy of from several microns up to 150 microns in thickness being deposited in a single application. If a thickness exceeding 100 microns is desired it is recommended that the coating be applied in two or several stages. Any single application should not be so thick that gravity forces exceed surface tension forces and cause flow of the liquid alloy to lower areas of the structure being coated.

For purposes of illustration and not limitation, the following are examples of metals and alloys which were readily and effectively surface coated utilizing the procedures and constituents disclosed above.

| Example No. | Underlying (Parent) Metal | | | Surface Coating | | |
|---|---|---|---|---|---|---|
| | Alloy | Hardness Vickers | Tarnish (1%NaS) | Alloy | Hardness Vickers | Tarnish (1%NaS) |
| 1. | Ag-Cu-Ge (71.1-27.6-1.3) | 95 | brown | 88Au-12Ge | 190–280 | nil |
| 2. | Ag-Cu-Ge (71.1-27.6-1.3) | " | brown | 94Au-6Si | 150–280 | nil |
| 3. | Ag-Cu-Ge (71.1-27.6-1.3) | " | brown | 80Au-20Sn | 150–250 | nil |
| 4. | Brass (70Cu-30Zn) | 75 | orange | 88Au-12Ge | 190–280 | nil |
| 5. | Brass (70Cu-30Zn) | " | orange | 94Au-6Si | 150–280 | nil |
| 6. | Brass (70Cu-30Zn) | " | orange | 80Au-20Sn | 150–250 | nil |
| 7. | Copper | 60 | black | 88Au-12Ge | 190–280 | nil |
| 8. | Mild Steel | 130 | nil | 88Au-12Ge | 190–280 | nil |

To further illustrate the present invention reference may be had to the drawings wherein.

Figure 1:
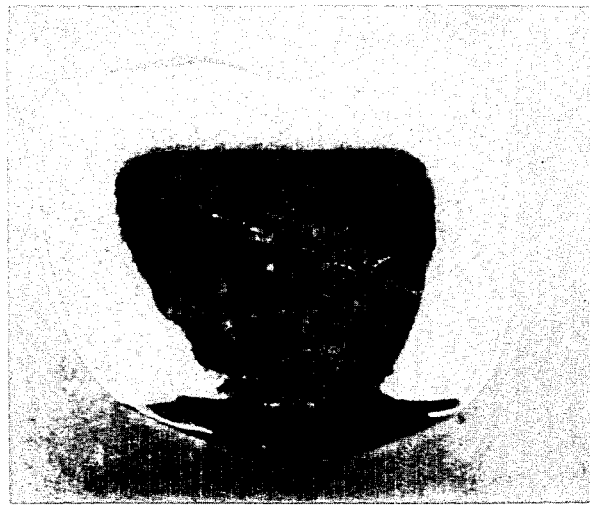
FIG. 1 is a photomicrograph of a dental crown, magnification X8.

With particular attention to FIG. 1, the dental crown as shown has been coated with the eutectic gold-germanium alloy containing 88% gold and 12% germanium by weight. The crown material is a silver-copper-germanium alloy such as that described in U.S. Pat. application Ser. No. 809,764, and would correspond to Example 1 of the present application. The polished cross-section of the crown has been exposed to a 1% sodium sulphide solution which has tarnished or etched the parent metal but not the gold alloy layer. The gold alloy coating is about 150 microns in thickness and is clearly distinguishable from the parent or underlying material.

Figure 2:
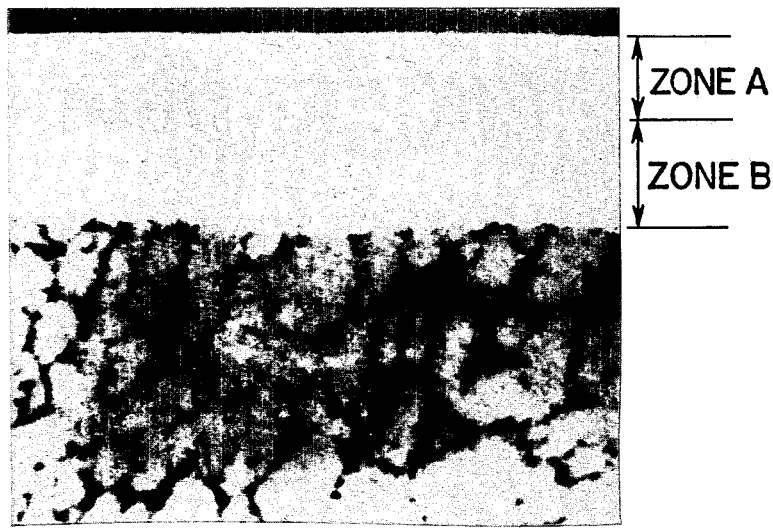
FIG. 2 is a photomicrograph of the gold layer of the wall of the crown of FIG. 1, having a magnification of X200.

FIG. 2 is a higher magnification of the gold layer of the wall of the crown of FIG. 1. The surface region of the gold layer shows the characteristic microstructure of eutectic gold-germanium alloy. The diffusion zone, zone B, where integral bonding is developed is about 75 microns in thickness and has the Vickers hardness of 160. The surface region of the gold alloy layer, zone A, has a thickness of about 70 microns and a Vickers hardness of 280. The parent metal has a Vickers hardness of 95.

By the present concept, one is able to employ an underlying or parent metal which may be chosen with respect to certain characteristic properties such as ease of casting and fabricating as well as being a low cost material. The thin surface layer of gold alloy which is integrally bonded to the underlying metal provides the hardness and corrosion resistance necessary for dental prostheses.

While the principals of the invention have been made clear with particular reference to certain preferred embodiments, it will be understood that variations and modifications can be effected by one skilled in the art within the spirit and scope of the invention.

The embodiments of the invention in which an exclusive property or privilege is claimed are defined as follows:

1. A process to provide an improved surface corrosion resistance and surface hardness to a substrate composed of a metal less noble than gold, which process comprises:
    (a) surface coating the less noble metal substrate with a slurry composed of (i) a gold alloy powder, said gold alloy having a melting point less than 600° C., (ii) an essentially inorganic oxide-dissolving flux which becomes fully active in a temperature range of about 550° C. to 600° C. and (iii) an organic liquid;
    (b) firing the slurry coating to a temperature of about 540° C. and above to melt and spread the gold alloy over the surface of the less noble underlying metal substrate.

2. The process of claim 1 wherein said gold alloy powder is composed of at least one of powdered binary gold alloys selected from the group consisting of gold-germanium, gold-silicon and gold-tin.

3. The process of claim 1 wherein said gold alloy consists essentially of from about 8 to 16% by weight germanium and the remainder gold.

4. The process of claim 1 wherein the gold alloy consists essentially of from about 3 to 9% by weight silicon and the remainder gold.

5. The process of claim 1 wherein the gold alloy consists essentially of from about 15 to 25% by weight tin and the remainder gold.

6. The process of claim 1 wherein the gold alloy powder and the oxide-dissolving flux are combined to form a powder composite containing up to 5% by weight of the oxide-dissolving flux and the remainder being gold alloy powder, the gold alloy being composed of at least one of the powdered binary gold alloys selected from the group consisting of gold-germanium, gold-silicon, and gold-tin.

7. The process of claim 1 wherein the organic liquid contains at least one of the constituents selected from the group consisting of ethylene glycol, cyclohexanol and ethyl or methyl alcohol.

8. The process of claim 1 wherein the organic liquid consists essentially of equal parts by volume of ethylene glycol, cyclohexanol and ethyl or methyl alcohol.

9. The process of claim 1 wherein the oxide-dissolving flux and organic liquid are combined to form an emulsion, the emulsion containing up to 15% by weight of the oxide-dissolving flux and the organic liquid containing at least one of the group consisting of ethylene glycol, cyclohexanol and ethyl or methyl alcohol.

10. The process of claim 1 wherein the slurry contains 5% maximum by weight of the oxide-dissolving flux, 15% maximum by weight of an organic liquid containing at least one of the constituents selected from the group consisting of ethylene glycol, cyclohexanol and ethyl or methyl alcohol and the remainder comprising at least one of a powdered binary gold alloy selected from the group consisting of gold-germanium, gold-silicon and gold-tin.

11. The process of claim 1 wherein the inorganic oxide-dissolving flux is composed principally of borates, carbonates, fluorides and chlorides of the alkali metals.

* * * * *